United States Patent
Oversluizen et al.

(10) Patent No.: US 11,045,661 B2
(45) Date of Patent: *Jun. 29, 2021

(54) PHOTOTHERAPY METHOD AND DEVICE

(71) Applicant: KONINKLIJKE PHILIPS N.V., Eindhoven (NL)

(72) Inventors: Gerrit Oversluizen, Valkenswaard (NL); Frank Anton Van Abeelen, Eindhoven (NL); Liesbeth Van Pieterson, Heeze (NL); Guofu Zhuo, Best (NL); Tim Dekker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 504 days.

This patent is subject to a terminal disclaimer.

(21) Appl. No.: 15/446,441

(22) Filed: Mar. 1, 2017

(65) Prior Publication Data

US 2017/0165498 A1    Jun. 15, 2017

Related U.S. Application Data

(63) Continuation of application No. 13/814,599, filed as application No. PCT/IB2011/053484 on Aug. 4, 2011, now Pat. No. 9,636,522.

(30) Foreign Application Priority Data

Aug. 11, 2010  (EP) ..................................... 10172544

(51) Int. Cl.
*A61N 5/00*    (2006.01)
*A61N 5/06*    (2006.01)

(52) U.S. Cl.
CPC ......... *A61N 5/0616* (2013.01); *A61N 5/0625* (2013.01); *A61N 2005/0628* (2013.01);
(Continued)

(58) Field of Classification Search
CPC ....... A61B 5/441; A61B 5/443; A61B 5/0616; A61B 5/0625; A61N 2005/0628;
(Continued)

(56) References Cited

U.S. PATENT DOCUMENTS

| 5,549,639 A | 8/1996 | Ross |
| 6,171,332 B1 | 1/2001 | Whitehurst |

(Continued)

FOREIGN PATENT DOCUMENTS

| WO | 2004033040 A1 | 4/2004 |
| WO | 2007106856 A2 | 9/2007 |

OTHER PUBLICATIONS

Hydrosun, http://www.hydrosun.de/en, Downloaded Sep. 10, 2015, 2 Pages.

(Continued)

*Primary Examiner* — Rex R Holmes
*Assistant Examiner* — Sana Sahand

(57) ABSTRACT

A method of biostimulating phototherapy is provided. The method comprises illuminating a subject's body portion with light having a first wavelength in the range of 600-900 nm. The method further comprises the step of at least one of reducing and preventing hyperthermia of the body portion by illuminating the body portion with light having a second wavelength which is at least one of in the range of 400-600 nm and in the range of 900-2500 nm. Further, a phototherapy device is provided which comprises a first light source and a second light source. The first light source is configured to emit light having a first wavelength which is in the range of 600-900 nm. The second light source is configured to emit light having a second wavelength which is at least one of in the range of 400-600 nm and in the range of 900-2500 nm. At least a portion of the device is a patch which is formed for conforming to at least part of the body (Continued)

portion. The device further comprises a sensor for sensing at least one skin property and a controller configured to operate at least the second light source as a function of the determined skin property.

13 Claims, 2 Drawing Sheets

(52) U.S. Cl.
CPC .............. *A61N 2005/0645* (2013.01); *A61N 2005/0651* (2013.01); *A61N 2005/0659* (2013.01); *A61N 2005/0662* (2013.01); *A61N 2005/0663* (2013.01)

(58) Field of Classification Search
CPC .... A61N 2005/0645; A61N 2005/0659; A61N 2005/0662; A61N 2005/0651; A61N 2005/0663; A61N 2005/0626; A61N 5/0616; A61N 5/0625
See application file for complete search history.

(56) References Cited

U.S. PATENT DOCUMENTS

| | | | |
|---|---|---|---|
| 9,327,138 B2* | 5/2016 | Jay | A61N 5/0617 |
| 9,901,746 B2* | 2/2018 | Wagenaar Cacciola | A61N 5/01 |
| 2003/0130709 A1* | 7/2003 | D.C. | A61N 5/0619 607/88 |
| 2003/0163068 A1* | 8/2003 | Kang | A61H 23/0245 601/15 |
| 2003/0167080 A1 | 9/2003 | Hart et al. | |
| 2003/0236487 A1 | 12/2003 | Knowlton | |
| 2004/0073079 A1 | 4/2004 | Altshuler et al. | |
| 2004/0162596 A1* | 8/2004 | Altshuler | A61N 5/0616 607/88 |
| 2005/0045189 A1 | 3/2005 | Jay | |
| 2006/0258896 A1 | 11/2006 | Haber et al. | |
| 2007/0060819 A1* | 3/2007 | Altshuler | A61B 5/0059 600/475 |
| 2007/0106856 A1* | 5/2007 | Nomura | G06F 11/1456 711/162 |
| 2007/0159592 A1* | 7/2007 | Rylander | A61B 5/0066 351/44 |
| 2007/0213792 A1 | 9/2007 | Yaroslavsky et al. | |
| 2008/0033516 A1 | 2/2008 | Altshuler et al. | |
| 2008/0319430 A1 | 12/2008 | Zenzie et al. | |
| 2009/0143773 A1* | 6/2009 | Gosse | A61B 90/98 606/12 |
| 2009/0254156 A1 | 10/2009 | Powell et al. | |
| 2010/0049180 A1 | 2/2010 | Wells et al. | |
| 2012/0116373 A1* | 5/2012 | Moench | A61B 18/203 606/9 |
| 2012/0172949 A1* | 7/2012 | Wagenaar Cacciola | A61N 5/06 607/90 |
| 2014/0288351 A1* | 9/2014 | Jones | A61N 5/06 600/9 |

OTHER PUBLICATIONS

Mark D. Shriver et al, "Comparison of Narrow-Bank Reflectance Spectroscopy and Tristimulus Colorimetry for Measurements of Skin and Hair Color in Persons of Different Biological Ancestry", American Journal of Physical Anthropology, vol. 112, No. 1, Apr. 13, 2000, pp. 17-27.

Hirotsugu Takiwaki, "Measurement of Skin Color, Practical Application and Tdheoretical Considerations", The Journal of Medical Investigation, vol. 44, Jan. 1, 1998, pp. 121-126.

T. Karu, "Primary and Secondary Mechanisms of Actions of Visible to Near-IR Radiation on Cells", J. Photochem Photobiol B 49 (1999) 1-17.

* cited by examiner

PHOTOTHERAPY METHOD AND DEVICE

CROSS-REFERENCE TO PRIOR APPLICATIONS AND CLAIM OF PRIORITY

This application claims the benefit or priority of and describes relationships between the following applications: wherein this application is a continuation of U.S. patent application Ser. No. 13/814,599, filed Feb. 6, 2013, which is the National Stage of International Application No. PCT/IB2011/053484, filed Aug. 4, 2011, which claims the priority of foreign application EP 10172544.8 filed Aug. 11, 2010, all of which are incorporated herein in whole by reference.

FIELD OF THE INVENTION

The present disclosure relates to biostimulating phototherapy, in particular to device and methods for dermatological phototherapy. The device and methods may be used both in professional and domestic use, and for curative, cosmetic and wellness purposes.

BACKGROUND OF THE INVENTION

Phototherapy is known and may take the form of applying light with one or more selected wavelengths to a subject's body to treat a condition or obtain a cosmetic effect. Examples are treatment for (neonatal) jaundice and psoriasis. In the art, methods and devices are sought to improve therapeutic efficiency.

WO 2004/033040 provides devices for modulating the efficacy and/or increasing the efficiency of treatment of disease and/or cosmetic conditions through photobiostimulation combined with heating and/or cooling of the treatment region. In one aspect, these devices are directed to modulating the efficacy of photobiostimulation in a target region by controlling the temperature in the region and/or its surrounding volume. According to some other aspects of the disclosed device, tissue is heated such that biostimulation is applied to tissue that is hyperthermic. Alternatively, portions of the target region can be cooled to selectively target biostimulation to a specific region at a desired depth below the skin surface. A feedback mechanism is also provided so that the temperature of the target region can be selectively and accurately controlled. The device may comprise a source of electromagnetic radiation generating radiation suitable for heating the target region so as to enhance the efficacy of biostimulation. To achieve photobiostimulation without hyperthermia a cooler, a cryogenic spray, or vaporizing cream is used.

However, inducing hyperthermia or hypothermia in tissue may be difficult to control accurately and it may not be available for certain groups of patients, e.g. patients with sensitive or damaged skin. It may also result in undesired side effects such as pain and tissue damage, in particular when a feedback mechanism for the temperature control malfunctions. The effects of hypothermia can be both negative and positive. Further, it has been found that clinical test results of photobiostimulating therapy are frequently inconclusive, which may be related to poor temperature control.

An improved method and device are therefore desired.

SUMMARY OF THE INVENTION

In one aspect, a method of biostimulating phototherapy is herewith provided. The method comprises illuminating a subject's body portion with light having a first wavelength in the range of 600-900 nm. The method further comprises the step of reducing and/or preventing hyperthermia of the body portion by illuminating the body portion with light having a second wavelength in the range of 400-600 nm and/or in the range of 900-2500 nm.

Light in the first wavelength range is considered beneficial for various treatments, both medically and cosmetic. Exemplary effects are stimulation of the mitochondrial respiratory chain (as discussed by T. Karu in J. Photochem Photobiol. B: Biol. 49 (1999) 1-17), pain treatment, sunburn prevention, wound healing, growth promotion, tissue restoration, reduction of scar formation and skin rejuvenation. Light in the first wavelength penetrates deep into the skin of a mammalian (in particular human) body portion and is absorbed in the dermis and hypodermic layers, which may lead to heating of the tissue.

Heating is considered compared to an average temperature of the body portion concerned. Generally, healthy human skin has a surface temperature of about 35-36° C. Temperatures above 38° C. are considered warm, above 42° C. is considered hot and pain and/or tissue damage may occur at temperatures of about 45° C. and higher. Temperatures above 38° C. are aimed to be prevented with the presently provided method and device.

Light of the second wavelength is predominantly absorbed by (melanin and water in) the epidermis of human skin. Thus, any heating of the skin due to absorption of the light at the second wavelength is concentrated in the epidermis, which is efficiently cooled by radiation off the skin and by convection along the skin. At the same time, the light of the second wavelength does substantially not penetrate into the dermis or hypodermic tissue. Direct heating of such deeper lying tissue is thus substantially prevented. Indirect heating of the dermis and hypodermic tissue by conduction from the epidermis occurs slower and is less efficient than direct heating. By appropriately controlling the intensity and dose of the applied light at the second wavelength, such indirect heating may be controlled and may substantially be prevented. Hence, illumination with light of the second wavelength may be used to generate only superficial heating of the skin, and substantially prevent heating of deeper-lying tissue.

It has been found that providing superficial heating of the skin is sufficient to trigger the heat sensors in the skin and incite physiologic thermal response processes such as vasodilatation and increase of blood perfusion through the skin and hypodermic tissue close to the skin.

Moreover, it has been found that light in the visible part of the second wavelength range, i.e. in the range 400-600 nm, in particular in the blue part thereof, i.e. in the range of about 400-500 nm, is perceived so well by human skin heat sensors that it may provide a sensation of warmth to the subject and trigger a physiologic thermal response even without actually heating the tissue.

Due to the increased blood flow through the body portion as a result of the thermal response, thermal load of the skin by the biostimulating light can be drawn off efficiently by the body and heating of the skin due to the biostimulating light can be mitigated. In other words, the thermal inertia of the skin is increased. Thus, by illuminating the body portion with light of the second wavelength, hyperthermia and associated complications can be reduced or even prevented. Further, higher intensities and/or doses of the first wavelength may be applied while maintaining a low tissue temperature than possible without increased perfusion. In addition, activity of the dermis is believed to be increased as a result of the thermal response. As a consequence, effectiveness and reliability of the therapy are increased.

Thus, it has been found that by applying optical energy to the skin of a body portion in the second wavelength, heating of the skin during phototherapy with the first wavelength may be controlled and the skin may even effectively be cooled, in particular in comparison to such phototherapy without illumination with light of the second wavelength.

Illumination with light in the blue part of the second wavelength range, 400-500 nm, has the added benefit of causing nitric oxide formation in the skin, which assists vasodilatation but which also is believed to reduce inflammation.

Illumination with the first wavelength may be continued during illumination with the second wavelength, so that both wavelengths may be applied concurrently. In this way, the beneficial effect of one wavelength may be maintained during application of the other wavelength.

A dose may comprise one or more pulses. Therefore, illumination with the first wavelength may comprise administering a series of pulses of the first wavelength.

A plurality of doses of the second wavelength may be administered to the body portion. Such method is particularly suitable with a prolonged phototherapy with light of the first wavelength range at a level which in itself is insufficient to maintain the thermal response at a desired level, as would typically be the case in Low Level Light Therapy (also known as "LLLT").

In a particular embodiment, the phototherapy comprises illuminating the body portion with a plurality of doses of the first wavelength and with a plurality of doses of the second wavelength. In the method, administration of at least a portion of the doses of the second wavelength is controlled to correspond to and precede administration of one or more doses at the first wavelength. Thus, a phototherapeutic regimen is provided with a series of pulse groups of one or more pulses at the first wavelength and one or more pulses at the second wavelength.

Administration of a dose of light may be timed as a function of one or more properties of (the skin of) the body portion, in particular in accordance with a detected and/or a predicted variation in one or more parameters of the body portion. Particular examples of such properties and associated parameters are the temperature of the body portion, and the relation between a variation in the intensity of the illumination with the first and/or second wavelength and associated (variation(s) in) the temperature and/or the thermal response.

The thermal response may depend on and be determined, inter alia, via (changes in) skin parameters such as the temperature of the skin and/or the hypodermic tissue and/or via (changes in) the skin color.

The temperature may be measured with any suitable thermometer, e.g. a contact thermometer, an optical thermometer and/or an invasive thermometer such as an intradermic or hypodermic thermometer.

Skin color and changes therein may be the consequence of, and thus may signal, vasodilatation, changes in blood flow and/or oxygenation, etc. Skin color may be measured and quantified using one or more parameters. Suitable parameters are provided by the melanin and erythema indices and by the L*a*b*-system of the Commission Internationale d'Éclairage (CIE). Suitable skin pigmentation measuring devices are commercially available for use in the field of cosmetics.

Also, a reflectometer may be used to determine the amount of illumination light that is reflected by the skin or the reflectance of the skin to determine or predict the amount of light that may be reflected by the skin at the first and/or second wavelength.

The method may thus comprise non-invasively determining an optical property of the skin of the subject's body portion, wherein the method comprises illuminating the body portion with the first wavelength at a first intensity and with the second wavelength at a second intensity and wherein at least one of the first intensity and the second intensity is determined as a function of the determined optical property.

The determined optical property may comprise at least one of the melanin index M and the lightness L* of the skin. This allows to determine the absorption of the skin of the illumination light which therefore allows to determine the optical power that is or will be deposited in the body portion at the first and/or second wavelength. Appropriately selecting the first intensity allows optimizing administration of the phototherapeutic dose. Appropriately selecting the second intensity allows optimizing administration of triggering the physiologic thermal response with little to no excess illumination. Further, this allows reducing power consumption in a treatment device.

The method may comprise administering the second wavelength at a deposited intensity of more than about 10 $mW/cm^2$ during illumination of the skin with the second wavelength and a time-averaged intensity of less than about 40 $mW/cm^2$. The intensity to be applied to the skin of the body portion may be equal to but will generally be higher than the deposited intensity. The deposited intensity may be determined by determining the applied irradiance at the skin and the intensity of the light that is reflected by the skin, and/or by determining the amount or concentration of absorbers in the skin at one or more wavelengths and calculating the absorption at the first and/or second wavelength. 10 $mW/cm^2$ input power is generally the lower level of what the skin receptors can detect as a heat input. 40 $mW/cm^2$ time averaged intensity is generally the power density that a healthy skin can absorb and lose via re-emission and/or convection, but which may lead to some heating. 20 $mW/cm^2$ time averaged intensity is generally acceptable for healthy skin with little to no temperature increase. The time averaged intensity is generally determined by averaging the intensity over a period of about 30 seconds to a minute and should be selected to substantially prevent heating by the light with the second wavelength, and in appropriate cases by the total illumination light of any wavelength.

In another aspect, a phototherapy device is herewith provided which may be used in the method described herein. The device comprises a first light source, and a second light source. The first light source is configured to emit light having a first wavelength which is in the range of 600-900 nm. The second light source is configured to emit light having a second wavelength which is in the range of 400-600 nm and/or in the range of 900-2500 nm. The device further comprises a sensor for sensing at least one skin property and a controller configured to operate at least the second light source as a function of the determined skin property. At least a portion of the device is formed to conform to at least part of the subject's body portion, e.g. by comprising a flexible, pliable or generally deformable portion such as a patch or bandage. The device being formed for conforming to at least part of the body portion to be treated improves user comfort and facilitates prolonged treatment. Such device, in particular in the form of a patch or bandage, may be worn inconspicuously under clothing. Such device allows improved and predictable illumination of the body portion since shifted illumination portions and/or shadows caused by relative movement of the device and the body portion are prevented.

In the device, the sensor may comprise a thermal sensor to detect and/or monitor temperature of (the skin of) the body portion. Such thermal sensor may be an intradermal thermometer but a non-invasive detector such as a contact thermometer or an optical thermometer etc. is preferred. The controller may be configured, e.g. programmed, to operate the second light source to illuminate the body portion with the second wavelength when the temperature of the body portion increases. Also, the controller may be configured, e.g. programmed, to operate the first light source. E.g., reducing the intensity of the first when the temperature of the body portion increases.

The sensor may be configured to determine at least one of the erythema index E and the a* value, allowing to control operation of the first and/or second light source as a function of the redness of skin signaling vasodilatation and/or otherwise increased blood perfusion.

The sensor may be configured to measure at least one of the melanin index M and the lightness L* of the skin of the subject's body part.

In an embodiment, the sensor may be configured to measure skin color, e.g. comprising a sensor that is capable of determination of more than one optical property of the skin, in particular determination of both melanin and erythema indices.

The sensor may comprise an intensity detector for detecting light emitted by the first light and/or the second light source and reflected from (the skin of) the body portion, allowing determination of the optical energy actually deposited in the body part.

The sensor may comprise a skin conductivity sensor, which allows to detect (variations in) sweating.

The controller may be configured to switch off the device but preferably it is configured to maintain the temperature, color and/or reflected intensity of at least a portion of the body portion at or below a particular desired value, e.g. by comprising one or more feedback loops.

The first and/or second light sources may comprise one or more light emitting diodes (LEDs). LEDs may provide light in various well-defined wavelengths (colors) at high efficiency and produce little heat compared to other light sources. The LEDs may therefore be placed close to the body portion. LEDs are generally well controllable with respect to output power and may be rapidly switched, enabling fine control over the operation of the device. Moderate and high-power LEDs that do not exhibit superluminous or laser operation are particularly suited for use in biostimulation since such LEDs do not exhibit a threshold-behavior in the emitted power and continuous power control is facilitated. A light source comprising plural LEDs facilitates a large effective surface area.

These and other aspects will hereafter be elucidated with reference to the figures of the drawings, which indicate examples for explanatory purposes only. Various other embodiments may be conceived within the scope of the appended claims.

BRIEF DESCRIPTION OF THE DRAWINGS

The above-described aspects will hereafter be more explained with further details and benefits with reference to the drawings showing an embodiment of the invention by way of example.

DETAILED DESCRIPTION OF EMBODIMENTS

Figure 1:
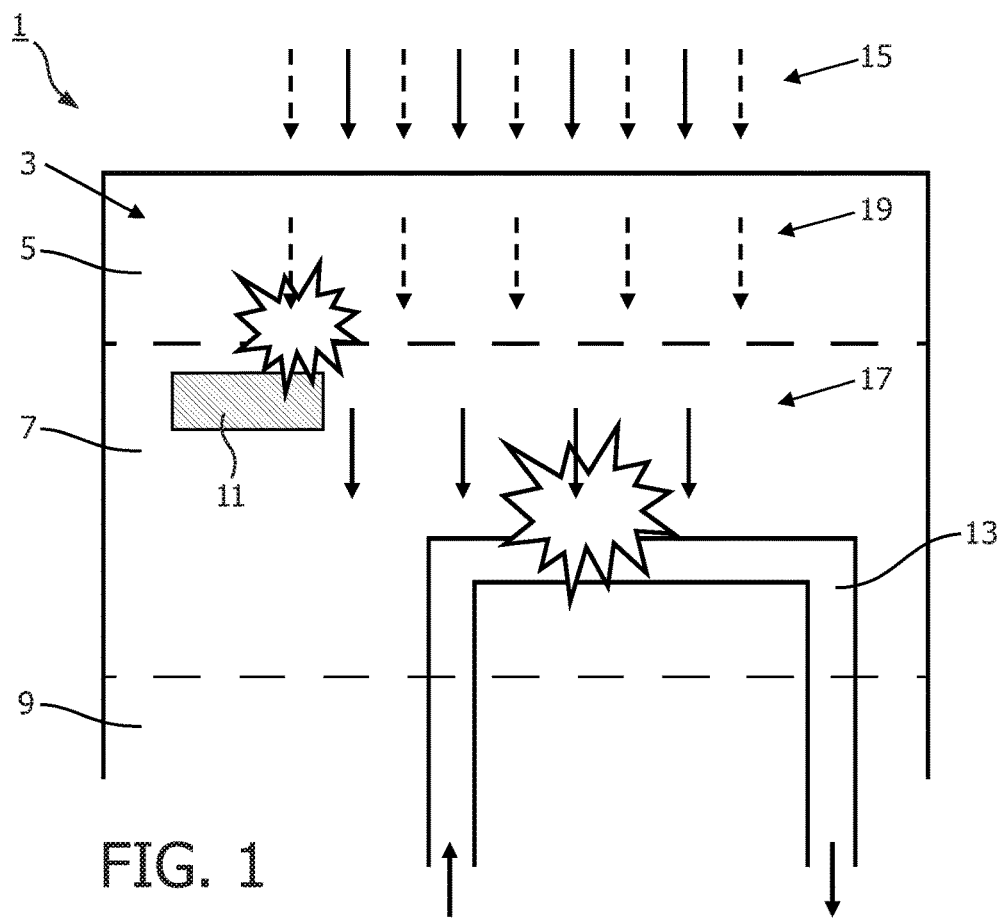
FIG. 1 is a schematic representation of a human body portion illuminated at two wavelengths.

It is noted that in the drawings, like features may be identified with like reference signs. It is further noted that the drawings are schematic, not necessarily to scale and that details that are not required for understanding the present invention may have been omitted. Further, elements that are at least substantially identical or that perform an at least substantially identical function are denoted by the same numeral.

FIG. 1 illustrates illumination of a human body portion 1, having a skin portion 3 which comprises an epidermis layer 5 of ca 0.1 mm thickness, and a ca 1-4 mm thick dermis layer 7 and which covers hypodermic tissue 9. In the dermis 7, and close to the epidermis 5, heat/cold sensors 11 are situated (only one shown). The dermis 7 further comprises capillary blood vessels 13 connected to larger blood vessels deeper in the body portion (not shown). FIG. 1 further shows illumination light 15, comprising light 17 having a first wavelength in a first range which is transmitted through the epidermis 5 and into the dermis 7 (or deeper, not shown) being absorbed there (indicated with a large star) and light 19 having a second wavelength in a second wavelength range which is transmitted into the epidermis 5 and is absorbed there (indicated with a small star).

In the epidermis, 5, the main optical absorbers are melanin and water. In the dermis 7, the main optical absorbers are water and blood. In the hypodermic tissue 9, the main optical absorbers are blood and lipids, which absorb mainly in the range 700-1100 nm. In the skin, scattering also occurs, the effects of which decreases with increasing wavelength.

Figure 2:
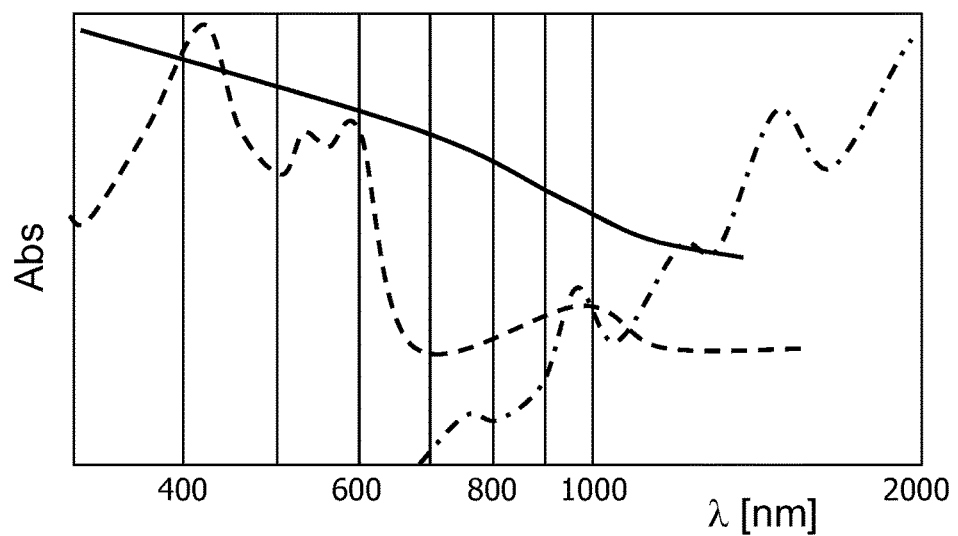
FIG. 2 is a schematic representation of absorption by absorbers in a human skin.
Figure 3:
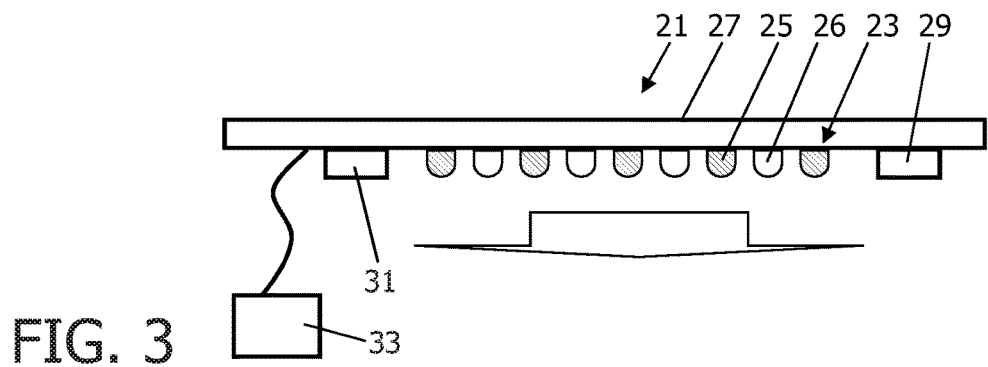
FIGS. 3-6 are schematic side view of different phototherapy devices.

FIG. 2 illustrates schematically the absorbance (log scale) of the main absorbers in the skin versus optical wavelength $\lambda$ (in nanometers): melanin (full line), (oxy)hemoglobin (dashed line) and water (dash-dotted line). Units of absorbance are generally given in $-\log_{10}(I/Io)$ with Io being the intensity incident on the absorber and I being the intensity transmitted through the absorber. The absolute values of the absorption of each absorber in a subject's body portion are determined by the local "composition" of the skin in terms of i.a. melanin content, water content, blood content and oxygenation of the blood. These values thus vary from subject to subject and generally also from point to point on a subject's body.

From FIG. 2 it will be clear that in the wavelength range 400-600 nm melanin is a main absorber and from about 950 nm onwards absorption is dominated by the combination of melanin and water. Thus, in the wavelength ranges 400-600 nm and 900-2500 nm absorption in the epidermis is important if not dominant. In the biostimulating wavelength range 600-900 nm the melanin in the epidermis 5 also absorbs a portion of the light which affects the energy actually deposited in the dermis 7 or hypodermic tissue 9.

Light 19 of the second wavelength excites the heat sensor 11, either directly or indirectly by heating the epidermis 5. Sufficient excitation of the heat sensors 11 in the skin triggers the physiologic thermal response of vasodilatation, increased blood flow, and possibly sweating. Doses of light 19 of the second wavelength may be applied in the form of a train of short high-intensity pulses at a high pulse repetition rate.

The melanin index M indicates the melanin content in the skin considered and the erythema index E is a measure of the redness of the skin. The lightness L* and the a* parameter are defined in 1976 by the Commission International d'Eclairage (CIE). L* is a measure of how the human eye perceives the lightness of the skin and a* is substantially a red/magenta parameter, see e.g. M. D. Shriver and E. J. Parra, Amer. J Phys Anthropology 112:17-27 (2000). It has been found that by determination of the melanin index or the lightness the optical absorption in the epidermis may be assessed. Hence, the actually administered phototherapeutic dose into the epidermis and into the deeper-lying tissue layers can be quantified. Similar holds for the erythema index or the a* parameter, which allow quantifying absorption at red wavelengths.

The melanin and erythema indices M and E may be measured by devices commonly used in cosmetic industry, e.g. the Skin Pigmentation Analyzer© SPA 99 of CK electronic GmbH, or the DSM II ColorMeter by Cortex Technology, which latter device can return the CIE parameters L*a*b* and the melanin and erythema indices M and E. Other parameters and/or units (e.g. RGB, CMYK color scales) may be used for quantifying skin color but these are considered less suitable and thus less preferred.

For determining epidermis absorption, measurement of the melanin index is preferred over measuring the lightness as being more a reliable parameter for quantifying the melanin content of the skin, see Shriver and Parra cited above. Other parameters and/or units (e.g. RGB, CMYK color scales) may be used for quantifying skin color but these are less suitable and thus less preferred.

The melanin concentration of the body portion and thus the melanin index and the lightness may, and generally will be, i.a. dependent on the body portion, the skin portion and the tanning of the skin portion. Further, the absorption and thus the filtering function of melanin are dependent on the wavelength of the used light. Considering such features allows providing an accurate prediction of the attenuation of an applied dose so that an illumination intensity and/or dose of phototherapeutic radiation to be administered may reliably be determined for depositing a desired intensity and/or dose of phototherapeutic radiation in the skin.

For such calculation a wavelength and melanin-index dependent irradiance correction factor Icf may be used with $Icf=Icf(M, \lambda)=\exp(Cm\, \mu(\lambda)\, d)$, wherein Cm is a measure of the concentration of melanosomes in the epidermis of the skin portion which may be stated in terms of the melanin index M as $Cm=(M-20)/150$ and may be approximated in terms of the lightness L* as $Cm=1.925-0.44\ln(L^*)$, $\ln(L^*)$ being the natural logarithm of L*. $\mu(\lambda)$ describes the wavelength dependent absorption of the melanin and may be approximated as $\mu(\lambda)=\mu_0 \lambda^{-3.33}=6.6\times10^{11}\, \lambda^{-3.33}$ in units of cm$^{-1}$ with $\lambda$ in units of nm and wherein $\mu_0$ to is the average absorption coefficient of a single melanosome. d accounts for the optical path in the epidermis. The thickness of the epidermis generally varies between about 0.04 mm to about 0.12 mm, taking scattering into account the value of d may be in a range from about 0.004 to about 0.024 cm, averaging over thickness variations and scattering provides a generally applicable range of about 0.008-0.016 cm, and a practical approximation is d=0.012 cm. The function Icf corresponds to the inverse of the attenuation of the radiation by melanin absorption and it provides an approximation of the filtering function of the skin under consideration for light to be transmitted through the melanin-containing tissue. The function Icf is applicable to usefully provide correction factors over a large wavelength range, from UV to near IR wavelengths, and for substantially all skin types, ranging from light Caucasian type skin to dark Negroid type skin.

In a particular case the intensity of a first wavelength $\lambda_1$ which is expected to be transmitted by the epidermis is $I_{trans}(\lambda_1)=I_{ill}(\lambda_1)/I_{ill}(\lambda_2)$, with $I_{trans}$ being the transmitted intensity and $I_{ill}$ being the illumination intensity. The intensity of the second wavelength which is expected to be absorbed by the epidermis is $I_{abs}(\lambda_2)=*(1-1/Icf(\lambda_2))$.

Advantageously, the melanin index or the lightness, respectively, is determined in a wavelength range between approx. 400 nm and approx. 2000 nm, in particular between approx. 600 nm and approx. 1200 nm, more in particular between approx. 600 nm and approx. 900 nm; since in the smaller ranges and in particular in the latter range effects of other absorbers are reduced.

FIGS. 3-6 show suitable phototherapy devices 21 for use in the above described method. The devices 21 comprise a first light source 25 for providing light at a first, biostimulating, phototherapeutic wavelength, and a second light source 26 for providing light at a second wavelength, mounted to a carrier 27, and a sensor 29. The devices of FIGS. 3-5 comprise a plurality of first and second light sources, collectively referred to as light sources 23. The sensor 29 may be configured for determining the melanin index of a subject's skin portion 3. The device 21 is arranged for illuminating the subject's skin portion 3 with light emitted by the light sources 23. The device further comprises a controller 31 connected with the sensor 29 for controlling operation of the light sources 23 as a function of a skin property determined by the sensor 29, e.g. the melanin index. The light sources 23 comprise light sources with different emission wavelengths (colors) and may comprise different emission spectra (spectral width, color range, color temperature etc.) which may be individually controllable. The first light sources 25 are configured to emit light with a wavelength in the range of 600 nm to 900 nm. The second light sources 26 are configured to emit light with a wavelength in the range of 400 nm to 600 nm, but may be configured to emit light with a wavelength in the range of 600 nm to 2500 nm.

The device 21 may be powered from any suitable power source 33, for portability powering from an accumulator or battery (not shown) is preferred. The controller 31 may comprise user operable knob with selectable settings. Also or alternatively, the controller may be configured to take additional input, e.g. for determining parameters of a therapy, user settings, timing, etc. Advantageously, the controller is arranged, programmable or programmed for controlling operation of the first and/or second light sources 25, 26 based on the Icf function discussed above. Such program may be stored on or in a memory comprised in the device 21.

The controller 31 may advantageously be configured for controlling operation of one or more of the light sources 23 during use, possibly automated, e.g. for adaptation to inadvertent skin heating or tanning etc.

Figure 4:
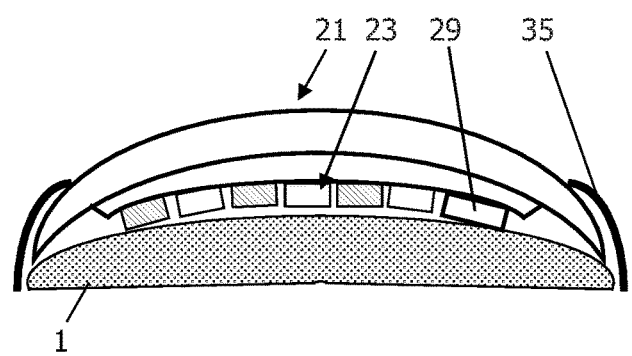

A portion of the phototherapy device 21 or the entire device 21 is formed as a human wearable patch, such as a device conforming to human physique, preferably being deformable or even pliable, indicated in FIG. 4. The patch may be maintained in position with any suitable means such as one or more adhesive portions, hook-and-loop-type fastener and/or a strap 35 closable around the body portion.

Alternatively (not shown) the method may be performed with a phototherapy device comprising an assembly comprising the light source, the sensor and/or the controller as separate objects, which may be interconnected for communicating with each other, e.g. with cables or via wireless communication.

A phototherapy device 21 may comprise plural sensors 29 for determining different properties of the subject's skin portion 3 and/or to detect local variations in a property of the skin portion. Advantageously, the first and/or second light sources 25, 26 comprise one or more Light Emitting Diodes or LEDs, which are available for numerous suitable wavelengths, provide significant optical output power per watt input power and generate little heat. Incoherent LEDs are considered particularly advantageous, since lasers require additional control, increasing complexity and cost of the device 21 and relatively narrowband radiation poses a high risk of overheating skin. Laser radiation may also present a danger to a users' eyes.

A skin color sensor 29 may comprise at least one light source and at least one detector for detecting light, the sensor being configured to illuminate a subject's skin portion 3 and detect light reflected off the subject's skin portion 3, wherein the sensor is configured for determining a reflectivity of the subject's skin portion at a plurality of wavelengths. This allows accurate determination of the reflectance of the skin portion contributions of different absorbers to the total skin absorption, allowing reliable determination of the intensities of the light at the first and/or second wavelengths.

In an embodiment, a sensor, e.g. a photodiode, is integrated in the device to measure the skin reflectance and/or absorbance of a user. A suitable dose for a specific application for the specific skin at a specific season or time can be obtained based on the real-time measurement results. A suitable photo-therapy scheme or algorithm may be automatically loaded from a pre-defined storage device or generated, possibly in real time, via e.g. a microprocessor that is attached to the device. In such way, an effective treatment may be reached with high comfort. Alternatively, an optimal algorithm may be selected by a user via a user interface on the device.

The light sources 23 may be at least partially surrounded or embedded in a padding material to increase user comfort. The device may be provided with a transparent wrapping or cover which may be washable. A disposable cover may increase hygiene.

Figure 5:
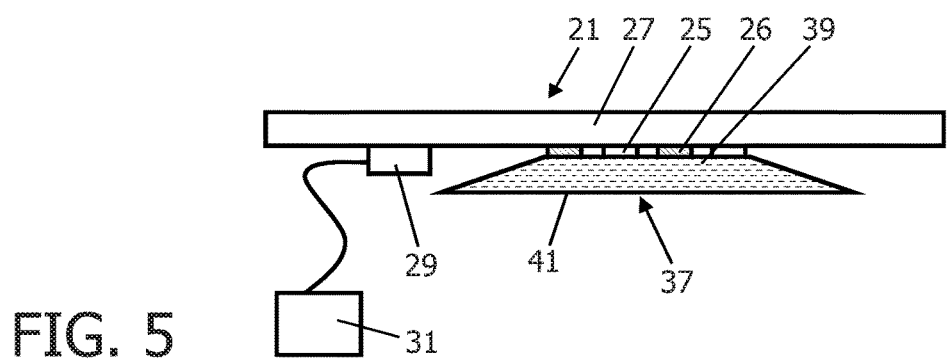

As another embodiment, FIG. 5 shows a patch 21 comprising surface-emitting LEDs 26 for emitting light with a wavelength of approx. 450 nm and surface-emitting LEDs 25 for emitting light with a wavelength of approx. 680 nm. The patch 27 further comprises a tapered light guide 37 having a first end 39 with a relatively small surface area for receiving light of the LEDs 25, 26 and a second end 41 with a relatively large surface area for re-emitting the light with a different, preferably more homogeneous intensity distribution.

Figure 6:
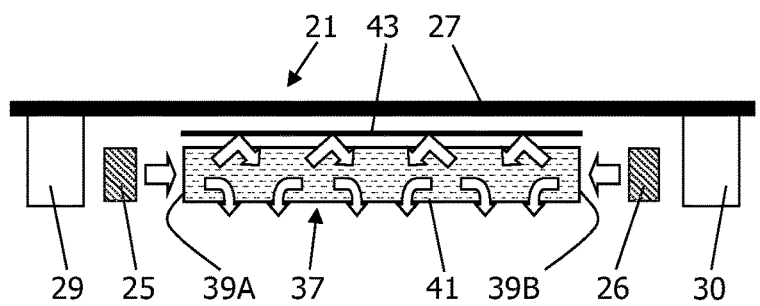

FIG. 6 illustrates another patch 21 comprising side-illumination of a flexible light guide 37 by one first light source 25 and one second light source 26 via opposite first ends 39A, 39B of the light guide 37. The first light source 25 is configured to emit light with a wavelength of approx. 820 nm and the second light source 26 is configured to emit light with a wavelength of approx. 500 nm. The light of the different wavelengths is scattered within the light guide 37, possibly being reflected by an optional reflector 43, to be emitted substantially homogeneously from the light guide 37 via second end 41 (see the open white arrows). The patch 21 comprises a first sensor 29 and a second sensor 30. The first sensor may be a skin color sensor and the second sensor 30 may be an optical thermometer.

A light guide 37 may comprise ridges, bumps or lens portions, also or alternatively, the light guide 37 may comprise one or more fiberoptic portions, e.g. one or more fiber bundles for redistributing the light. The light guide 37 may comprise silicone incorporating absorption or reflection particles, fabrics or any other material that is translucent or transparent at the used wavelengths. An intensity redistributing light guide 37 may improve homogeneity of the illumination and/or assist illuminating a relatively large skin surface area from a relatively small light emitting surface.

Other variations to the disclosed embodiments can be understood and effected by those skilled in the art in practicing the claimed invention, from a study of the drawings, the disclosure, and the appended claims. Features from different embodiments may be suitably combined within the scope of the appended claims, unless explicitly mentioned otherwise. "Light emitting diode" or LED includes "organic light emitting diode" or OLED. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:
1. A phototherapy device comprising:
a combined light source comprising a first light source and a second light source,
wherein the first light source is configured to emit a first light,
wherein the first light has a first wavelength,
wherein the first wavelength is in a range of 600-900 nm,
wherein the second light source is configured to emit a second light,
wherein the second light has a second wavelength,
wherein the second wavelength is in at least one of a range of 400-600 nm and a range of 900-2500 nm,
wherein the first light and the second light are emitted toward a portion of a user's skin;
a sensor, wherein the sensor is configured to determine at least one of a melanin index (M) and a lightness (L*) of the user's skin; and
a controller circuit configured to operate the first wavelength at a first intensity and the second wavelength at a second intensity,
wherein the sensor provides at least one of a melanin index (M) and a lightness (L*) of the user's skin to the controller circuit,
wherein at least one of the first intensity and the second intensity is a function of the at least one of a melanin index (M) and a lightness (L*)
wherein the controller circuit is configured to determine a melanin-index dependent irradiance correction factor (Icf) as:

$Icf = \exp(Cm\mu(\lambda)d,$ wherein Cm is a measure of the concentration of melanosomes in an epidermis of the skin portion, wherein Cm is determined based on one of the melanin index and the lightness, wherein $\mu(\lambda)$ relates to wavelength dependent absorption of melanin, wherein d relates to an optical path in the epidermis wherein the controller circuit is arranged to adjust at least one of an intensity and a dose of a portion of the combined light source based on the melanin-index dependent irradiance correction factor.

2. The phototherapy device of claim 1, wherein the sensor is configured to determine at least one of an erythema index (e) and a red/magenta parameter (a*) value of the skin.

3. The phototherapy device of claim 1, wherein the sensor is further configured to determine one of an optical property of the skin and a thermal property of the skin.

4. The phototherapy device of claim 1, wherein the sensor comprises at least one of a thermal sensor, an intensity sensor and a conductivity sensor.

5. The phototherapy device of claim 4, wherein the intensity sensor is configured to detect light emitted by at least one of the first light source reflected from the skin and the second light source reflected from the skin.

6. The phototherapy device of claim 1, wherein the wavelength of the second light source is in a blue part of the second wavelength range.

7. The phototherapy device of claim 1, wherein the second light source is operated with an intensity of at least 10 mW/cm2 and with a time average intensity of at most 40 mW/cm2.

8. The phototherapy device of claim 1, wherein the controller circuit operates the second light source prior to operating the first light source.

9. The phototherapy device of claim 1, wherein the light emitted from the first light source and the second light source are emitted as a plurality of doses, wherein each of said doses comprises one or more pulses.

10. A non-transitory computer-readable storage-medium, the medium modified by control information including instructions which, when executed by a phototherapy device cause the device to execute the functions of:

operating a first light source to emit a first light,
wherein the first light source has a first wavelength,
wherein the first wavelength is in a range of 600-900 nm;

operating a second light source to emit a second light,
wherein the second light source has a second wavelength,
wherein the second light source is in at least one of a range of 400-600 nm and a range of 900-2500 nm;

controlling the first light source to illuminate a subject's skin with the first light and the second light;

sensing to determine a melanin-index dependent irradiance correction factor (Icf) of the skin;

sensing a temperature of a portion of the subject's skin that is illuminated;

adjusting at least one of an intensity and a dose of the light of at least one of the first wavelength and the second wavelength based on the melanin-index dependent irradiance correction factor; and adjusting the illumination of at least one of the first light and the second light based on a temperature of the skin, wherein the second light source is activated as the temperature of the subject's skin changes, wherein the melanin-index dependent irradiance correction factor (Icf) is determined by:

$$Icf = \exp(Cm\mu(\lambda)d,$$

wherein Cm is a measured of the concentration of melanosomes in an epidermis of the skin and is determined based on one of a melanin index and a lightness of the skin, wherein $\mu(\lambda)$ relates to wavelength dependent absorption of melanin, wherein d relates to an optical path in the epidermis.

11. The non-transitory computer-readable storage-medium of claim 10, wherein the second light source is operated prior to operating the first light.

12. The non-transitory computer-readable storage-medium of claim 10, further configured to execute the instructions to determine at least one of an erythema index (e) and a red/magenta parameter (a*) value of the skin.

13. The non-transitory computer-readable storage-medium of claim 10, further configured to execute the instructions to determine one of: an optical property of the skin and a thermal property of the skin.

* * * * *